United States Patent [19]

Niswender

[11] 3,983,099
[45] Sept. 28, 1976

[54] THYROXINE- AND TRIIODOTHYRONINE-TYROSINE DIPEPTIDE DERIVATIVES

[75] Inventor: Gordon Dean Niswender, Fort Collins, Colo.

[73] Assignee: Micromedic Diagonistics, Inc., Horsham, Pa.

[22] Filed: Mar. 19, 1975

[21] Appl. No.: 559,862

[52] U.S. Cl. ........................... 260/112.5 R; 424/1.5; 260/559 A
[51] Int. Cl.$^2$ ................. C07G 103/52; C07G 7/00
[58] Field of Search ................ 260/112.5 R, 559 A; 424/177

[56] References Cited
UNITED STATES PATENTS 3,715,434  2/1973  Mende ......................... 260/112.5 R

*Primary Examiner*—Lewis Gotts
*Assistant Examiner*—Reginald J. Suyat
*Attorney, Agent, or Firm*—Terence P. Strobaugh; Carl A. Castellan; George W. F. Simmons

[57] ABSTRACT

The present invention is concerned with the production of novel derivatives of thyroid hormones which are useful in the radioimmunoassay (RIA) of such hormones. The invention is particularly concerned with derivatives of thyroxine and triiodothyronine which contain an additional phenol group which is readily iodinatable so that the phenol conjugate can be readily tagged with a radioactive iodine isotope, such as $^{125}$I or $^{131}$I, without detrimentally interfering with the ability of the tagged conjugate so competitively bind with the naturally occurring thyroid hormone in the biological liquid to be analyzed by RIA technique. The invention is also concerned with the iodine-tagged derivatives or conjugates.

9 Claims, No Drawings

THYROXINE-AND TRIIODOTHYRONINE-TYROSINE DIPEPTIDE DERIVATIVES

DESCRIPTION OF THE INVENTION

Heretofore, in the RIA of the thyroid hormones, they have been radioactively labeled by replacing one or more of the inactive iodine atoms present in thyroxine (hereinafter sometimes referred to by the designation $T_4$) and in triiodothyronine (sometimes herein referred to by $T_3$) as they occur naturally with a radioactive isotope, e.g. $^{125}I$ or $^{131}I$. The interchange reaction, however, is time-consuming, troublesome, and expensive; it requires extreme care and is generally unreliable. It generally provides a low yield of a product having low specific activity.

In accordance with the present invention, novel thyroid hormone conjugates are provided which retain the ability to competitively bind on a binding protein, such as thryoxine binding globulin, or on an antiobody which is specific to corresponding thyroid hormones of the type from which the conjugates are made. The new compounds are those of the formula:

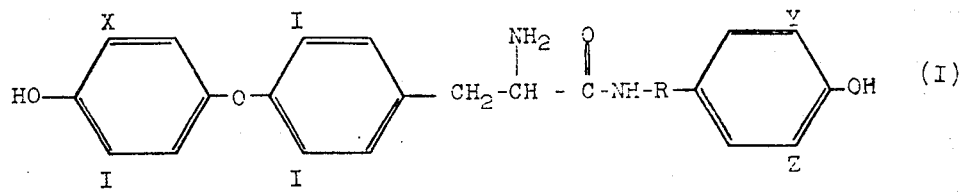

wherein
X is H, I, $^{125}I$, or $^{131}I$,
R is a group selected from the group consisting of a. 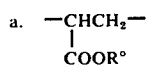

wherein R° is a alkyl group, such as one having up to 18 carbon atoms, preferably 1 to 2 carbon atoms, and

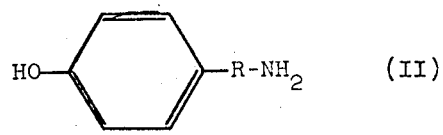

in which R is an alkylene group having 1 to 18, preferably 1 to 3 carbon atoms which may be substituted with an element or group other than an amino or unesterified carboxylic acid group.

Examples of the compounds that may be so used are:
p-(aminomethyl)phenol
p-(β-aminoethyl)phenol(tyramine)
p-(3-aminopropyl)phenol
p-(2-aminopropyl)phenol One of the preferred groups of compounds that may be so used are the alkyl esters of tyrosine having the formula:

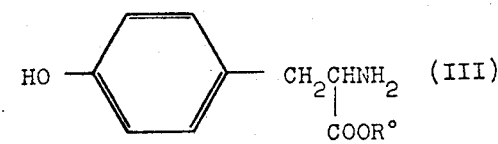

wherein R° is an alkyl group having from 1 to 18, preferably from 1 to 2 carbon atoms, such as the methyl or ethyl ester of tyrosine.

The preferred reactant compounds are tyramine and that of Formula III wherein R° is methyl. These compounds serve to introduce a phenolic group having both ortho positions (with respect to the hydroxyl group) available and receptive to halogenation.

In general the reaction of the $T_3$ or $T_4$ with the aminoalkyl-containing phenol of Formula II or III is carried out in a solvent medium containing a tertiary amine at a low temperature in the range of about 0° to 20° C. A small amount of a chloroformic acid ester of a lower alkanol having 1 to 4 carbon atoms is used as a self-regenerating intermediate that serves as a reaction-facilitating vehicle or interchanging agent by forming an anhydride with the $T_3$ or $T_4$ respectively that hydrolyzes in the presence of the amine of Formula II or III, which, in turn, results in the formation of an amide of the $T_3$ or $T_4$ monocarboxylic acid, the amide linkage serving to couple or conjugate a phenolic ring to the $T_3$ or $T_4$ molecule respectively. A preferred chloroformate is the isobutyl ester which forms an anhydride that is particularly prone to hydrolyze under the conditions of the reaction. The amine of Formula II or III is added after the chloroformate has reacted. Then an inorganic alkaline material, e.g., caustic soda or potash, is added.

The reaction may be illustrated by the following sequence of steps, using R'COOH to represent the $T_3$ or $T_4$ molecule,

as the chloroformate ester, and R'''NH₂ as the amine of Formula II or III:

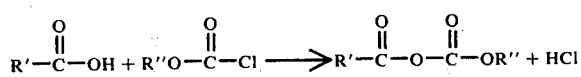

-continued

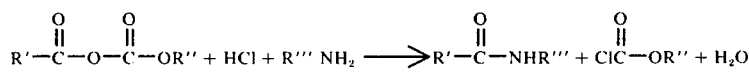

Thus, the product has a hydroxyphenyl group linked to the $T_3$ or $T_4$ molecule through an amidoalkyl linkage connected to the newly-combined phenyl group in the position para to the phenolic hydroxyl thereon. It may be, and hereinafter it is sometimes, called a $T_3$-phenol or $T_4$-phenol conjugate.

The resulting $T_3$- or $T_4$- derivative (phenol conjugate) is readily iodinated to introduce one of the radioactive iodine isotopes (e.g. $^{125}I$ and $^{131}I$) into one or both of the two positions of the phenolic group ortho to the hydroxyl group. Such iodination, for example, can be effected by mixing the $T_3$- or $T_4$-phenol conjugate in an aqueous solution of sodium iodide in which the anion is one of the radioactive isotopes of iodine, such as mentioned above, and an oxidizing agent, such as Chloramine T. Optionally, but preferably, the aqueous reaction medium is buffered at a pH of 6 to 8, preferably about 7.4. After completion of the reaction, a reducing agent is added to enutralize any residual oxidizing agent and the iodinated $T_3$- or $T_4$-phenol conjugate is then separated from free radioactive iodine, as by electrophoresis or column chromatography.

For use in RIA procedures, thyroxine ($T_4$) and/or triiodothyronine ($T_3$) is covalently bonded with a protein of sufficiently high molecular weight, such as from 10,000 to 300,000 or even up to a million or more, to convert the $T_3$ or $T_4$ (normally a hapten) into an antigen that can be injected into the blood stream of a vertebrate, such as a rabbit, hamster, or sheep, to develop an antibody that is specific for $T_3$ or $T_4$ and can be used in an RIA procedure to assay body fluids for their content of $T_3$ or $T_4$.

Examples of protein that can be covalently bonded with the $T_3$ or $T_4$ by reaction with the carboxylic group thereof include blood proteins generally having molecular weights in the range of 3 million to 20 million, and the globulins, albumins, and fibrinogens having molecular weights in the range of 100,000 to a million. Specifically, bovine serum albumin, sheep serum albumin, rabbit serum albumin, goat serum albumin, polysine, thyroglobulin, and gamma-globulin may be used.

The same general procedure described above for making the $T_3$- or $T_4$-phenol conjugate can be used for making the $T_3$- or $T_4$- protein conjugate from the $T_3$ or $T_4$ using the protein in place of the amine of Formula II or III.

The following procedures are illustrative of the present invention. In these procedures, the temperatures are in centigrade and the letter u of the English alphabet is used in place of the customary Greek letter $\mu$ to represent the prefix "micro" when placed before an abbreviation of a unit of measure.

EXAMPLE 1

Preparation of the compound of Formula I wherein X is iodine, Y and Z are H, and R is $$-\underset{\underset{COOCH_3}{|}}{C}HCH_2-,$$

the thyroxine conjugate of methyl ester of tyrosine ($T_4$-TME conjugate)

Fifty mg. of thyroxine and 40 ml. of tri(n-butyl)amine are dissolved in 1.5 ml. of anhydrous dimethylformamide (DMF) in a suitable container, such as a glass test tube, beaker, or flask, and the solution is cooled to 10° C. Twenty-five ml. of isobutyl chloroformate is added to the solution, and the mixture is stirred for 20 minutes at 10°C. Then, a solution of 40 mg. of the hydrochloride salt of the methyl ester of tyrosine (TME.HCl) in 7.5 ml. of water and 7.5 ml. of DMF plus 250 ml. of 1N NaOH is added in one portion. The resulting reaction mixture is stirred while cooling the container in an ice bath and the mixture is allowed to come to room temperature, e.g., by standing overnight. The resulting clear solution is poured into 40 ml. of ice water, extracted twice using two 20 ml. portions of ethyl acetate (i.e., 2 × 20 ml. ethyl acetate). The ethyl acetate solution obtained from combining both extractions is washed as follows:

3 × 20 ml. in 1N $NaHCO_3$

3 × 20 ml. 1N HCl

2 × 20 ml. $H_2O$

The washed product is dried over anhydrous $CaSO_4$ (e.g., Drierite), filtered and stripped on a rotary evaporator. After triturating with ether-hexane (1:1), filtering and drying, 75 mg. of solid product (80% yield) of Formula I (in which X is I, Y and Z are H, and R is $$-\underset{\underset{COOCH_3}{|}}{C}HCH_2-$$

is obtained.

Thin liquid chromatography (TLC) on silica gel in methylene chloride:acetone (80:20) shows a single spot with an Rf factor greater than thyroxine and less than tyrosine methyl ester.

EXAMPLE 2

The product of Example 1 ($T_4$-TME) is labeled with $^{125}I$ in the following manner:

To 2.5 ug of the product, there is added (1) 50 ul of 0.5M phosphate buffer containing 1 mCi of $Na^{125}I$ and (2) 30 ug Chloramine T. (The buffer solution to which the $Na^{125}I$ is added consists of 34 g of $KH_2PO_4$ and 35.5 g. of anhydrous $Na_2HPO_3$ per liter of water.) The reaction mixture is agitated for 30 seconds and then 60 ug of sodium metabisulfite is added. The iodinated conjugate ($^{125}I$-$T_4$-TME in which $^{125}I$ replaces Y and/or Z of Formula I) is then separated from free $^{125}I$ by column chromatography. The average number of tagged iodine atoms ($^{125}I$) in the molecule is found to be 1.2.

EXAMPLE 3

The tyrosine methyl ester (TME) conjugate of triiodothyronine ($T_3$), i.e., the compound of Formula I in which X, Y, and Z are H and R is

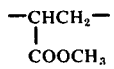

is prepared as follows:

Forty mg. of T$_3$ and 16 ul. of tri-(n-butyl)amine are dissolved in 1 ml. of DMF in a glass vessel and the solution is cooled to 10° C. Nine ul. of isobutyl chloroformate is added and the mixture stirred for 20 min. at 10°. At this time a solution of 16 mg. TME.HCl in 2.5 ml. water and 2.5 ml. of dimethylformamide plus 100 ul. of 1N NaOH are added in 1 portion. The reaction mixture is stirred while the vessel is held in an ice bath, and allowed to come to room temperature overnight. The clear solution is poured into 30 ml. of ice water, extracted with two 15 ml. portions of ethyl acetate and the ethyl acetate extract is washed with:

3 × 15 ml. 1N NaHCO$_3$

3 × 15 ml. 1N HCl

2 × 15 ml. H$_2$O

The product is dried over anhydrous CaSO$_4$ (e.g. Drierite), filtered and stripped on a rotary evaporator. After triturating with ether-hexane (1:1), filtering and drying, the resultant solid product weighs 50 mg. (a 92% yield of the compound of Formula I in which X, Y, and Z are H, and R is the same as in Example 1).

TLC on silica gel in methylene chloride:acetone (80:20) shows a single spot with an Rf factor greater than triiodothyronine and less than tyrosine methyl ester.

EXAMPLE 4

Preparation of $^{125}$I-T$_3$-TME

The product of Example 3 (T$_3$-TME) is labeled with $^{125}$I in the following manner:

To 2.5 ug of the product, there is added (1) 50 ul of 0.5M phosphate buffer containing 1 mCi of Na$^{125}$I and (2) 30 ug Chloramine T. (The buffer solution to which the Na$^{125}$I is added consists of 34 g. of KH$_2$PO$_4$ and 35.5 g. of anhydrous Na$_2$HPO$_4$ per liter of water.) The reaction mixture is agitated for 30 seconds and then 60 ug of sodium metabisulfite is added. The iodinated conjugate ($^{125}$I-T$_3$-TME in which $^{125}$I replaces the hydrogen atoms of Y and/or Z (and possibly of X) of Formula I) is then separated from free $^{125}$I by column chromatography. The amount of Na$^{125}$I used herein is sufficient to replace at least one H, probably in the Y or Z position.

EXAMPLE 5

T$_4$-Tyramine

Follow the procedure of Example 1; 30 mg. of the hydrochloride salt of tyramine (tyramine.HCl) is used in place of 40 mg of TME.HCl to prepare the T$_4$-tyramine conjugate of Formula I wherein X is I, Y and Z are H, and R is ethylene.

EXAMPLE 6

$^{131}$I-T$_4$-Tyramine

Follow the procedure of Example 2; T$_4$-Tyramine obtained in Example 5 is used in place of T$_4$-TME and Na$^{131}$I is used in place of Na$^{125}$I to prepare the corresponding $^{131}$I-T$_4$-Tyramine in which $^{131}$I replaces one or both hydrogen atoms in the Y and Z positions of Formula I.

EXAMPLE 7

T$_3$-Tyramine

Follow the procedure of Example 3; 12 mg. of tyramine.HCl is used in place of 16 mg of TME.HCl to prepare the T$_3$-Tyramine conjugate of Formula I wherein X, Y, and Z are H and R is ethylene.

EXAMPLE 8

$^{125}$I-T$_3$-Tyramine

Follow the procedure of Example 4; T$_3$-Tyramine obtained in Example 7 is used in place of T$_3$-TME to prepare $^{125}$I-T$_3$-Tyramine in which $^{125}$I replaces the hydrogen atoms of Y and/or Z (and possibly of X) of Formula I. The amount of Na$^{125}$I used herein is sufficient to replace at least one H, probably in the Y or Z position.

EXAMPLE 9

T$_4$-Tyrosine n-butyl Ester

Follow the procedure of Example 1; 49 mg. of the hydrochloride salt of the n-butyl ester of tyrosine is used in place of 40 mg. of TME.HCl to prepare the T$_4$-tyrosine n-butyl ester conjugate of Formula I wherein X is H, Y and Z are H, and R is

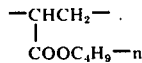

EXAMPLE 10

T$_3$-Tyrosine n-butyl Ester

Follow the procedure of Example 3; 20 mg. of the hydrochloride salt of the n-butyl ester of tyrosine is used in place of 16 mg. of TME.HCl to prepare the T$_3$-tyrosine n-butyl ester conjugate of Formula I wherein X, Y, and Z are H and R is

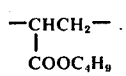

EXAMPLE 11

T$_4$-Tyrosine Lauryl Ester

Follow the procedure of Example 1; 67 mg. of the hydrochloride salt of the lauryl ester of tyrosine is used in place of 40 mg. of TME.HCl to prepare the T$_4$-tyrosine lauryl ester conjugate of Formula I wherein X is I, Y and Z are H, and R is

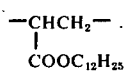

EXAMPLE 12

T$_3$-Tyrosine Lauryl Ester

Follow the procedure of Example 3; 27 mg. of the hydrochloride salt of the lauryl ester of tyrosine is used in place of 16 mg. of TME.HCl to prepare the T$_3$-tyrosine lauryl ester conjugate of Formula I wherein X, Y, and Z are H, and R is

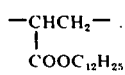

EXAMPLE 13

T$_4$-Tyrosine Octadecyl Ester

Follow the procedure of Example 1; 82 mg. of the hydrochloride salt of the octadecyl ester of tyrosine is used in place of 40 mg. of TME.HCl to prepare the T$_4$-tyrosine octadecyl ester conjugate of Formula I wherein X is I, Y and Z are H, and R is

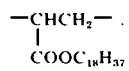

EXAMPLE 14

T$_3$-Tyrosine Octadecyl Ester

Follow the procedure of Example 3; 33 mg. of the hydrochloride salt of the octadecyl ester of tyrosine is used in place of 16 mg. of TME.HCl to prepare the T$_3$-tyrosine octadecyl ester conjugate wherein X, Y, and Z are H and R is

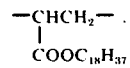

EXAMPLE 15

T$_4$-p(4-aminobutyl)phenol

Follow the procedure of Example 1; 35 mg. of the hydrochloride salt of p(4-aminobutyl)phenol is used in place of 40 mg. of TME.HCl to prepare the T$_4$-p(4-aminobutyl)phenol conjugate of Formula I wherein X is I, Y and Z are H, and R is butylene.

EXAMPLE 16

T$_3$-p(4-aminobutyl)phenol

Follow the procedure of Example 3; 14 mg. of the hydrochloride salt of p(4-aminobutyl)phenol is used in place of 16 mg. of TME.HCl to prepare the T$_3$-p(4-aminobutyl)phenol conjugate of Formula I wherein X, Y, and Z are H, and R is butylene.

EXAMPLE 17

T$_4$-p(8-aminooctyl)phenol

Follow the procedure of Example 1; 45 mg. of the hydrochloride salt of p(8-aminooctyl)phenol is used in place of 40 mg. of TME.HCl to prepare T$_4$-p(8-aminooctyl)phenol conjugate of Formula I wherein X is I, Y and Z are H, and R is octylene.

EXAMPLE 18

T$_3$-p(10-aminodecyl)phenol

Follow the procedure of Example 3; 20 mg. of the hydrochloride salt of p(10-aminodecyl)phenol is used in place of 16 mg. of TME.HCl to prepare the T$_3$-p(10-aminodecyl)phenol conjugate.

EXAMPLE 19

T$_4$-p(18-aminooctadecyl)phenol

Follow the procedure of Example 1; 69 mg. of the hydrochloride salt of p(18-aminooctadecyl)phenol is used in place of 40 mg. of TME.HCl to prepare the T$_4$-p(18-aminooctadecyl)phenol conjugate.

EXAMPLE 20

T$_3$-p(18-aminooctadecyl)phenol

Follow the procedure of Example 3; 28 mg. of the hydrochloride salt of p(18-aminooctadecyl)phenol is used in place of 16 mg. of TME.HCl to prepare the T$_3$-p(18-aminooctadecyl)phenol conjugate.

EXAMPLE 21

Iodination with $^{125}$I

The products of Examples 9–20 are iodinated following the procedure of Example 2. The derivatives of T$_4$ give products where the hydrogen atoms of Y and/or Z in Formula I are replaced by $^{125}$I. The derivatives of T$_3$ give products where the hydrogen atoms of Y and/or Z in Formula I are replaced by $^{125}$I and with sufficient additional Na$^{125}$I the hydrogen of X is also partly or completely replaced.

EXAMPLE 22

Iodination with $^{131}$I

Na$^{131}$I can be used in place of Na$^{125}$I to prepare products corresponding to those of Example 21.

EXAMPLE 23

Preparation of 3,3′,5-triiodothyropropionic acid-BSA, i.e. the Bovine Serum Albumin Conjugate of T$_3$ (triiodothyronine)

a. 317 mg (0.5 mmole) of triiodothyronine and 0.125 ml (0.5 mmole) tri-n-butylamine are dissolved in 5 ml of dry dioxane and cooled to 10°C. Then 0.66 ml (0.5 mmole) of isobutylchloroformate is added and the reaction is allowed to proceed at 4°C for 20 minutes. This mixture is then added in one portion to a well-stirred and cooled solution of 0.7 gram (0.006 mmole) BSA in 37 ml of 1:1 water:dioxane and 0.7 ml of 1N NaOH. After 1 hour, an additional 0.33 ml of 1N NaOH is added and the mixture is stirred at 4°C for a total of 4 hours. After dialyzing for 48 hours in running water, the murky mixture is centrifuged and the clear supernatant is made acid to pH 4.6 with 0.1 N HCl. The precipitate is separated by centrifugation, suspended in 60 ml of water, and brought into solution at pH 8.5 with 0.1 N NaOH. This is dialyzed overnight and then lyophilized. Yield 800 mg (80%).

b. A sample of the conjugate obtained in part a) is prepared at a concentration of 45 mg/liter in 0.05 M "tris" buffer, pH 8.5. This "tris" buffer solution contains 3.4 g. KH$_2$PO$_4$ and 3.55 g anhydrous Na$_2$HPO$_4$ in 1 liter of water. The estimated degree of conjugation is 20 moles of T$_3$ per mole of BSA by differential absorbance in the U.V. at 290.

EXAMPLE 24

Preparation of thyroxine-BSA Conjugate (i.e. T$_4$-BSA)

a. 380 mg (0.5 mmole) of thyroxine and 0.125 ml (0.5 mmole) tri-n-butylamine are dissolved in 5 ml of dry dioxane and cooled to 10°C. Then 0.66 ml (0.5 mmole) of isobutyl chloroformate is added and the reaction is allowed to proceed at 4°C for 20 minutes. This mixture is then added in one portion to a well-stirred and cooled solution of 0.7 gram (0.006 mmole) BSA in 37 ml of 1:1 water:dioxane and 0.7 ml of 1N NaOH. After 1 hour, an additional 0.33 ml of 1N NaOH is added and the mixture is stirred at 4°C for a total of 4 hours. After dialyzing for 48 hours in running water, the murky mixture is centrifuged and the clear supernatant is made acid to pH 4.6 with 0.1 N HCl. The precipitate is separated by centrifugation, suspended in 60 ml of water, and brought into solution at pH 8.5 with 0.1 N NaOH. This is dialyzed overnight and then lyophilized. Yield 800 mg (75%).

b. A sample of the above conjugate obtained in part (a) is prepared at a concentration of 45 mg/liter in 0.05 M tris buffer, pH 8.5. The estimated degree of conjugation is 20 moles thyroxine per mole of BSA by differential absorbance in the U.V. at 290.

EXAMPLE 25

RIA Determination of $T_3$

For RIA determination of $T_3$, the following solutions and blood sera are used:

A. 0.4 M barbital buffer solution which contains 54.4 grams of sodium acetate and 82.8 grams of sodium barbital dissolved in 1 liter of water.

B. 8.5 percent sodium chloride solution which contains 85 grams of sodium chloride dissolved in one liter of distilled water.

C. 0.08 M barbital buffer solution prepared by mixing 200 milliliters of solution A with 80 milliliters of solution B and adjusting the pH to 8.6 with concentrated hydrochloric acid. The resulting solution is diluted to a volume of 1 liter with distilled water. 100 milligrams of sodium azide is added as a stabilizing agent.

D. Barbital buffer solution with 0.05 M EDTA which contains 200 milliliters of solution A and 80 milliliters of solution B mixed with 16.8 grams of ethylenediaminetetra-acetic acid, disodium salt. The EDTA is brought into solution by heating and then cooling to room temperature. The pH is adjusted to 8.6 with either hydrochloric acid or sodium hydroxide as appropriate and the solution is then diluted to 1 liter with distilled water.

E. Barbital buffer solution with 0.1 percent gelatin made by adding 1 gram of gelatin to 1 liter of buffer C above and heating with stirring until the gelatin is in solution.

F. ANS solution which contains 2 milligrams of 8-anilino-1-naphthalene sulfonic acid (ANS) per milliliter in buffer E above.

G. First antibody serum against $T_3$ obtained from the diluted serum of a rabbit that has been injected with the product of Example 23.

H. Normal rabbit serum obtained from a rabbit which has not been inoculated with the hapten to be assayed.

I. Normal rabbit serum diluted by mixing one part by volume of serum in H above with 100 parts by volume of buffer D.

J. A solution of the first antibody serum (G above) at a dilution of one part by volume per 1000 obtained by diluting one part of antibody solution G above with 100 parts by volume of buffer D solution and then diluting one milliliter of the resulting diluted solution with nine milliliters of the diluted solution obtained in I above.

K. A solution in buffer C of $T_3$-tyrosine methyl ester conjugate tagged by iodination (Ex.4). The $^{125}$I-$T_3$-TME has a gamma ray radioactivity of 30,000 to 50,000 counts per minute.

L. A second antibody serum obtained from the blood serum of a sheep injected with the gamma globulin of a normal rabbit.

M. Second antibody solution prepared by diluting the antibody serum of L above 1:35 with buffer D.

N. Human blood serum taken from a person whose $T_3$ level is to be determined.

O. Antibody complex prepared by mixing 50 microliters of first antibody solution of J above with 200 microliters of second antibody solution of M above. This mixture must be, and is, allowed to stand at least 2 hours before use in the assay.

The following procedure is used to assay for $T_3$ using standard RIA techniques:

1. A mixture is made of 100 microliters of human blood serum N to be tested with 150 microliters of ANS solution F plus 250 microliters of buffer C plus 100 microliters of $^{125}$I-$T_3$-TME K. Vortex.

2. Add 250 microliters of antibody mixture O. Vortex.

3. Incubate at room temperature for two hours.

4. Add 3 milliliters of buffer C and centrifuge at 1000 X-g for 30 minutes.

5. Pour off supernatant. The resulting solid product is then subjected to radioactivity detection as by means of a gamma counter.

EXAMPLE 26

RIA Determination of $T_4$

For RIA determination of $T_4$, the solutions and blood sera designated by (A), (B), (C), (D), (E), (F), (H), (I), (L), and (M) in Example 25 are used. In addition the following are used.

$G^1$. First antibody serum against $T_4$ obtained from the diluted serum of a rabbit that has been injected with the product of Example 24.

$J^1$. A solution of the first antibody in $G^1$ above at a dilution of 1 part by volume per 1000 obtained by diluting one part of antibody solution $G^1$ above with 100 parts by volume of buffer D solution and then diluting 1 milliliter of the resulting diluted solution with 9 milliliters of the diluted solution obtained in I above.

$K^1$. A solution in buffer C of $T_4$-tyrosine methyl ester conjugate tagged by iodination (Ex.2). The $^{125}$I-$T_4$-TME has a gamma ray radioactivity of 30,000 to 50,000 counts per minute.

$N^1$. Human blood serum taken from a person whose $T_4$ level is to be determined.

$O^1$. Antibody complex prepared by mixing 50 microliters of first antibody solution of $J^1$ above with 200 microliters of second antibody solution of M above. This mixture must be and is allowed to stand at least 2 hours before use in the assay.

The following procedure is used to assay for $T_4$ using standard RIA techniques:

1. A mixture is made of 100 microliters of human blood serum $N^1$ to be tested with 150 microliters of ANS solution F plus 250 microliters of buffer C plus 100 microliters of $^{125}$I-$T_4$-TME $K^1$. Vortex.

2. Add 250 microliters of antibody mixture $O^1$. Vortex.

3. Incubate at room temperature for 2 hours.

4. Add 3 milliliters of buffer C and centrifuge at 1000 X-g for 30 minutes.

5. Pour off supernatant. The resulting solid product is then subjected to radioactivity detection as by means of a gamma counter.

The other $T_3$ conjugates and $T_4$ conjugates of the preceding examples from 1 through 22 are useful for assay purposes in essentially the same way as in Examples 25 and 26.

We claim:

1. A compound of the formula

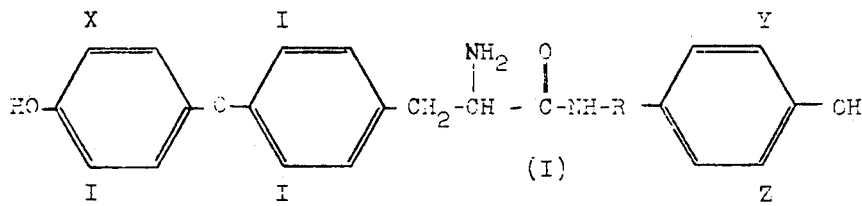

wherein
X is H, I, $^{125}$I, or $^{131}$I,
R is a group selected from the group consisting of a. 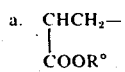

wherein R° is an alkyl group, and
b. an alkylene group,
Y is H; $^{125}$I, or $^{131}$I, and
Z is H; $^{125}$I, or $^{131}$I.

2. A compound according to claim 1 in which R° is a butyl group.

3. A compound according to claim 1 in which R is an ethylene group.

4. A compound according to claim 1 wherein X is I and R is

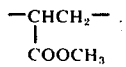

5. A compound according to claim 4 wherein at least one Y or Z radical is $^{125}$I or $^{131}$I.

6. A compound according to claim 1 wherein X is H and R is

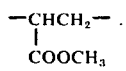

7. A compound according to claim 6 wherein at least one of the Y and Z radicals is $^{125}$I or $^{131}$I.

8. A compound according to claim 2 wherein at least one of the Y and Z radicals is $^{125}$I or $^{131}$I.

9. A compound according to claim 3 wherein at least one of the Y and Z radicals is $^{125}$I or $^{131}$I.

* * * * *

UNITED STATES PATENT AND TRADEMARK OFFICE
CERTIFICATE OF CORRECTION

PATENT NO. : 3,983,099
DATED : September 28, 1976
INVENTOR(S) : Gordon Dean Niswender It is certified that error appears in the above-identified patent and that said Letters Patent are hereby corrected as shown below:

Column 1, line 20 - "antiobody" should be -- antibody --.

Column 1, line 44 - "a" should be -- an --.

Column 1, line 45 - add:

(b) an alkylene group, such as one having 1 to 18 carbon atoms, preferably an alkylene group having 1 to 3 carbon atoms, Y is H; $^{125}I$, or $^{131}I$, and Z is H; $^{125}I$, or $^{131}I$.

The new compounds wherein both Y and Z are H regardless of whether X is H or iodine, are readily iodinatable to introduce a radioactive iodine isotope in either or both of the Y and Z positions (and also in the X position if desired, when X is H The resulting radioactive derivatives are thyromimetic at least to the extent of competitively binding wi

UNITED STATES PATENT AND TRADEMARK OFFICE
CERTIFICATE OF CORRECTION

PATENT NO. : 3,983,099
DATED : September 28, 1976
INVENTOR(S) : Gordon Dean Niswender It is certified that error appears in the above-identified patent and that said Letters Patent are hereby corrected as shown below:

PAGE 2 of 2 thyroxine ($T_4$) and/or triiodothyronine ($T_3$) on a binding protein, such as a thyroxine-binding globulin, or on an antibody generated in the blood stream of a vertebrate by an antigenic protein conjugate of thyroxine or of triiodothyronine, so that the products of the present invention are quite useful in the determination of $T_3$ and/or $T_4$ by competitive protein binding assay (CPBA) or by radioimmunoassay (RIA).

The compounds of Formula I in which Y and Z are hydrogen and X is hydrogen or iodine of unradioactive nature are produced by reacting $T_3$ or $T_4$ respectively with a paraaminoalkyl phenol to introduce an additional phenolic group into the $T_3$ or $T_4$ molecule. The reactant that may be so used may be a compound of the general formula:

Signed and Sealed this

Eighth Day of February 1977

[SEAL]

Attest:

RUTH C. MASON
*Attesting Officer*

C. MARSHALL DANN
*Commissioner of Patents and Trademarks*